United States Patent
Walker et al.

[11] Patent Number: 5,989,261
[45] Date of Patent: Nov. 23, 1999

[54] EVALUATING THE FIT OF AN ORTHOPAEDIC IMPLANT

[75] Inventors: Peter Stanley Walker, Middlesex, United Kingdom; John Nevil Insall, New York, N.Y.; Jonathan Blamey; Michael Wadcock, both of Wiltshire, United Kingdom; Mark Alan Heldreth, Mentone, Ind.; Shawn Elliott McGinley, Forth Wayne, Ind.; Steven A. Zawadzki, Leesburg, Ind.

[73] Assignee: Zimmer, Ltd., United Kingdom

[21] Appl. No.: 08/898,360

[22] Filed: Jul. 29, 1997

[30] Foreign Application Priority Data

Mar. 13, 1997 [GB] United Kingdom ............... 9705172

[51] Int. Cl.⁶ .......................................... A61F 2/28
[52] U.S. Cl. ............... 606/102; 606/88; 606/85; 623/20
[58] Field of Search .................. 606/79, 85, 86, 606/87, 88, 102; 623/16, 18, 20

[56] References Cited

U.S. PATENT DOCUMENTS

| | | | |
|---|---|---|---|
| 4,791,919 | 12/1988 | Elloy et al. .................. | 606/62 |
| 5,344,423 | 9/1994 | Dietz et al. . | |
| 5,344,461 | 9/1994 | Phlipot . | |
| 5,395,377 | 3/1995 | Petersen et al. . | |
| 5,472,415 | 12/1995 | King et al. . | |
| 5,609,642 | 3/1997 | Johnson et al. ............ | 623/20 |

FOREIGN PATENT DOCUMENTS

| | | |
|---|---|---|
| 689 796 A1 | 1/1996 | European Pat. Off. . |
| 554 959 B1 | 12/1996 | European Pat. Off. . |
| 9705161 | of 0000 | United Kingdom . |
| 2 280 375 | 2/1995 | United Kingdom . |
| WO 96/25123 | 8/1996 | WIPO . |

*Primary Examiner*—Michael Buiz
*Assistant Examiner*—David O. Reip
*Attorney, Agent, or Firm*—Burns, Doane, Swecker & Mathis

[57] ABSTRACT

The invention provides means for evaluating the fit of a knee replacement prosthesis on a resected tibial surface. A provisional instrument for this purpose includes a positioning tray having a peripheral profile corresponding to that of the tibial platform of the prosthesis, the tray having an upper surface and an under surface which is substantially flat and free from projections and the tray having a plurality of holes for receiving pins for temporarily attaching the positioning tray in a desired position on the resected tibial surface. Also disclosed is a jig for guiding, drilling and broaching operations, the jig having an aperture which is shaped to guide the broach. In addition, the invention includes a tibial broach which includes a hollow body having an upper end and a lower end and having an anvil at its upper end, an interior face and a posterior face which slopes downwardly towards a lower end, the posterior face having a series of teeth which are formed in the hollow body, such that bone cut by the teeth as the broach is driven into an intramedullary canal of a tibia passes into the hollow body.

4 Claims, 6 Drawing Sheets

EVALUATING THE FIT OF AN ORTHOPAEDIC IMPLANT

FIELD OF THE INVENTION

This invention relates to means for evaluating the fit of a corresponding orthopaedic implant and for fitting such an implant to a bone. One aspect of the invention is concerned with provisional instruments for the installation of knee replacement prostheses.

In another aspect the invention is concerned with a novel design of broach for shaping a canal in a tibia to receive a knee implant.

BACKGROUND OF THE INVENTION

Total knee replacement prostheses of the condylar type comprise a femoral component, a tibial base plate and a plastics meniscal component arranged to support the femoral component, and to be mobile to a limited extent on the base plate. One typical prosthesis of this kind is described in UK Patent Application No. 2280375. Accurate and rapid fitting of orthopaedic implants is facilitated by the use of suitable instruments so that the prosthesis, when installed, operates in the way in which it is designed.

It is an important consideration in fitting a knee prosthesis that the tibial base plate should be fixed on the strongest portion of resected bone, should not twist within the bone and that, when fixed, the joint should articulate in the most effective manner.

SUMMARY OF THE INVENTION

According to one aspect of the present invention there is provided a provisional instrument component for evaluating the fit of a knee replacement prosthesis which comprises a positioning tray having a peripheral profile corresponding to that of the tibial platform of the prosthesis, the tray having an under surface which is substantially flat and free from projections, and said tray having a plurality of holes for receiving pins for temporarily attaching the positioning tray in a desired position on a resected tibial surface.

DETAILED DESCRIPTION OF THE INVENTION

In use, the positioning tray can be moved around by the surgeon on the end of the resected tibia to select the optimum position for providing support to the eventual tibial platform. When the surgeon has selected an optimum position, the positioning tray is temporarily secured to the resected bone with pins through the locating holes. These pins are positioned towards the lateral and medial sides of the positioning tray so as not to obscure the area which will ultimately receive the tibial stem.

Preferably, the positioning tray carries an upstanding boss which is receivable within a recess in a provisional plastics component. The surgeon may then fit a provisional or final femoral component and test the movement of the plastics component on the provisional tray. The boss referred to above may also include means for engagement with an extractor tool. For example, it may be threaded for attachment to an extractor tool.

The provisional tray may then be removed for the next stage in the fitting process. Headless fixing pins may be employed at this point so that the tray can be removed, leaving the pins upstanding from the resected bone.

After removal of the provisional tray, the next stage is to place over the resected bone a jig for forming a hole in the intramedulary canal for receiving the stem of the tibial platform. For this purpose, a similarly shaped tray to the provisional tray may be provided, having holes which correspond to the pins upstanding from the resected bone. This second tray will, however, include a shaped central opening for receiving a guide for a drill and/or a broaching tool. Using the drill and/or the broaching tool, a hole is then made for the tibial stem. The jig and broach are then removed as well as the upstanding pins.

The next stage is then to fit a tibial tray with a stem. At this point, a provisional tibial tray may be fitted having a stem but no anterior abutment. This platform then enables the surgeon to test the movement of various sizes of plastics and femoral components before making the final selection.

BRIEF DESCRIPTION OF THE DRAWINGS

Other advantages and features of the present invention will become apparent with reference to the accompanying drawings, in which.

DESCRIPTION OF PREFERRED EMBODIMENTS

Figure 1A:
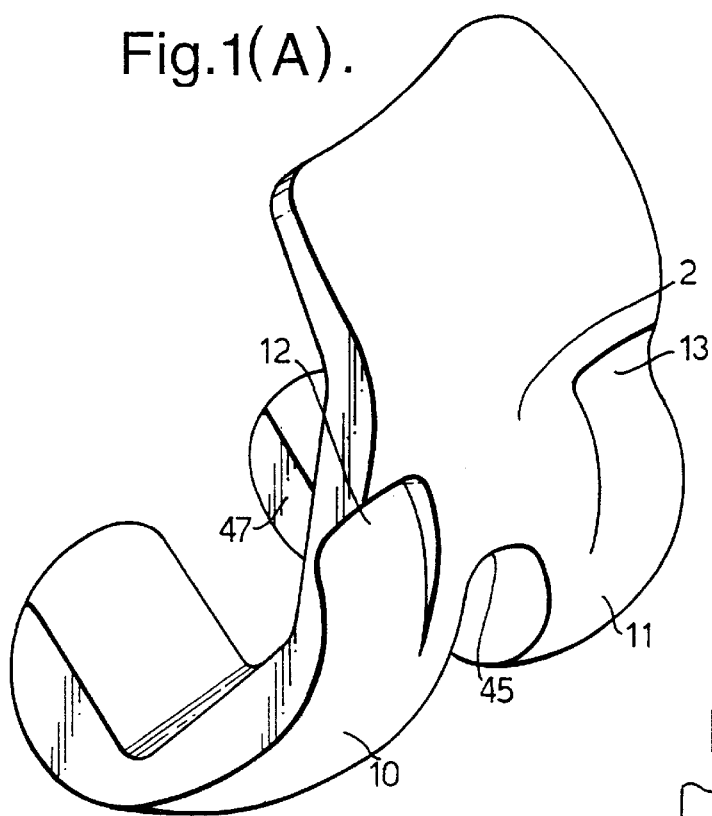
FIG. 1(A) is a perspective view of a femoral component of the prosthesis.
Figure 1B:
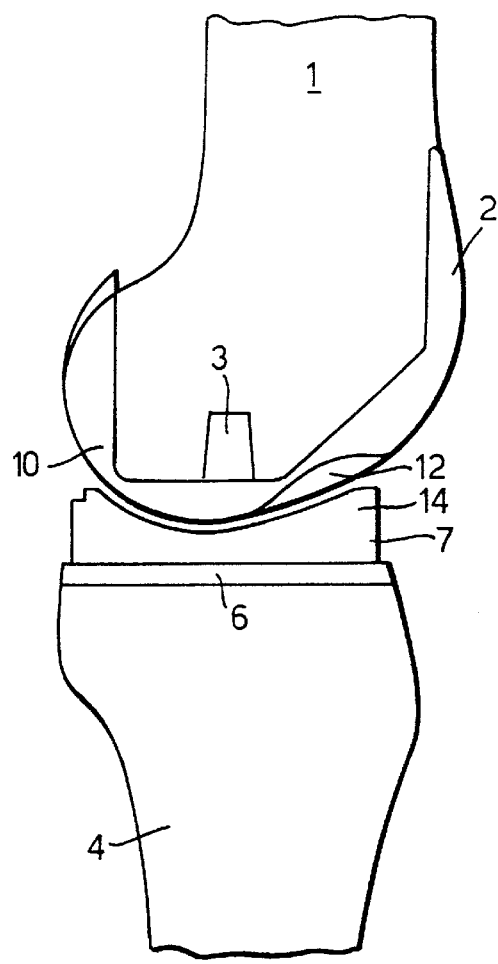
FIG. 1(B) is a side elevation showing the prosthesis in assembled form.

Referring to the accompanying drawings, FIG. 1(B) shows the femur 1 resected to provide a base for receiving a femoral component 2, which is retained in the resected femur by pins 3. The head of the tibia 4 is also resected to provide a surface to which a tibial component 6 is fitted. The resected surface on the tibia is usually inclined by a small angle, e.g. 5–7°, to the vertical axis of the tibia. Meniscal plastics component 7 is interposed between the tibial component 6 and the femoral component 2. As best seen in FIGS. 1(A) and 1(B), the femoral component 2 has condylar surfaces 10 and 11 (which are preferably spheroidally shaped) and which articulate within corresponding depressions 41 and 42 (see FIG. 3) in meniscal component 7 and, in so doing, cause the meniscal component 7 to move in an anterior/posterior (A-P) direction on the upper surface 20 of the tibial component.

Figure 2:
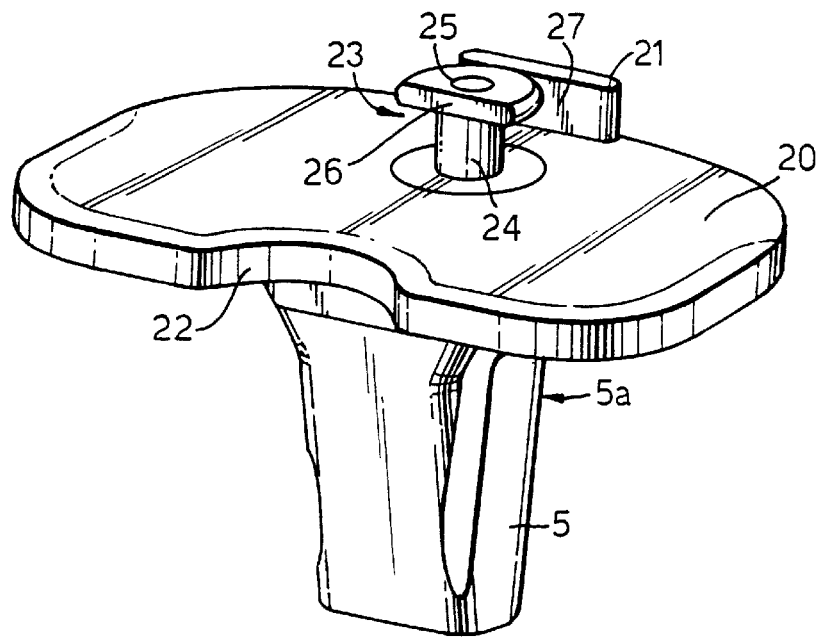
FIG. 2 is a perspective view of the final tibial component.
Figure 3:
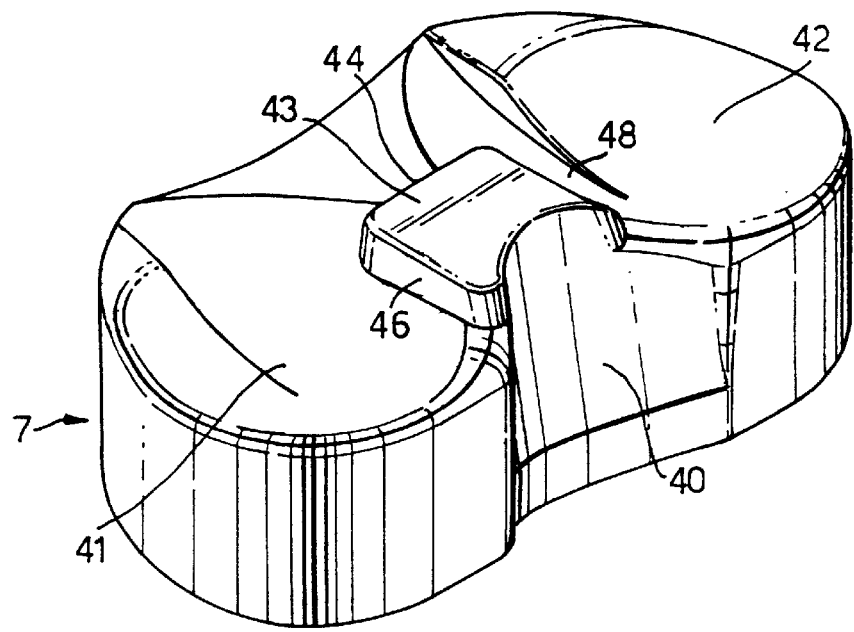
FIG. 3 is a perspective view of the final plastics meniscal component.

The detailed construction of the tibial component is shown in FIG. 2 and of the meniscal bearing component in FIG. 3.

As can be seen from FIG. 2, the tibial component comprises a generally flat platform 20 supported on a stem 5 which is intended for introduction into the intramedullary canal of the tibia. Upstanding from the anterior face of the tibial platform is a rail 21, which provides an anterior positive stop for the anterior displacement of the meniscal component 7 on the tibial platform 20.

The posterior side of the tibial platform is cut away at 22 to allow for retention of the posterior cruciate ligament and an upstanding guide 23 is provided for retaining the meniscal component on the tibial platform and for guiding the plastics meniscal component for limited sliding and pivoting movement on the platform 20. The guide 23 comprises a post 24 and a cap 25. The cap 25 is fixed to the top of the post and has a flat face 26 in a posterior direction which is substantially parallel to the face 27 of the anterior stop. Preferably, the cap is D-shaped. Further details of the construction of the prosthesis are given in UK Patent Application No. 2280375 and in UK Patent Application No. 9705161.9, filed Mar. 13, 1997, the disclosure of both of which applications is specifically incorporated hereby by reference.

Fitting of the tibial component will now be described with reference to FIGS. 4, 5, 6 and 7.

Figure 4:
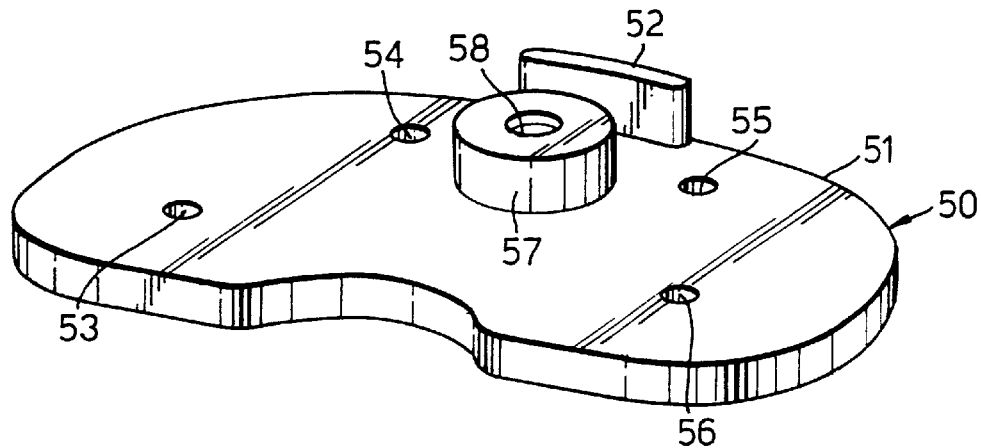
FIG. 4 is a perspective view of a tibial sizing and positioning tray.

Referring to FIG. 4, this shows a tibial sizing and positioning tray 50 which comprises a plate 51 having an outer periphery substantially corresponding to the profile of the tibial tray 20 shown in FIG. 2. The positioning tray 50 also has an anterior stop 52, which is positioned in the same relative position as the anterior rail 21 in the tibial component shown in FIG. 2. Plate 51 has locating holes 53 to 56 which extend through the plate 51. Plate 51 also carries a boss 57, having a generally cylindrical shape and an internal thread 58.

The positioning tray is used in the following way. As a first step, the tibia 4 is resected and a flat surface cut on its top. This can be achieved using a variety of instruments and guides. For example, the instruments described in U.S. Pat. No. 5,395,377 or European Patent Application No. 0689796 (U.S. patent application Ser. No. 265,884 filed Jun. 27, 1994). Alternatively, the top of the tibia can be milled to provide a flat continuous surface using the guide and milling machine described in European Patent Application No. 0554959 (U.S. patent application Ser. No. 832,098, filed Feb. 6, 1992).

Having achieved a flat surface to the top of the tibia, the surgeon takes the tray 50 and moves it around the head of the tibia to find a position where he judges there will be minimal sinkage of the eventual tibial platform into the bone in use. Having selected the desired position from this aspect, pins are inserted through holes 53 to 56 in order to temporarily locate the plate on the resected head of the tibia.

A meniscal component similar to that shown in FIG. 3, but with a recess suitable for receiving the boss 57 without a snap fit (but with the same A-P freedom of movement as the final meniscal component), is then placed on top of the plate. Using this provisional plastics component the surgeon can move the plastics component to see how it articulates on the top of the platform when engaged with the femoral component. Having satisfied himself that the platform will provide a satisfactory position, the positioning tray is removed. This can be done by lifting off the tray if the pins employed through holes 53 to 56 are headless, or it can be removed with an extractor tool screwed into threaded hole 58 if headed pins are employed.

Figure 6:
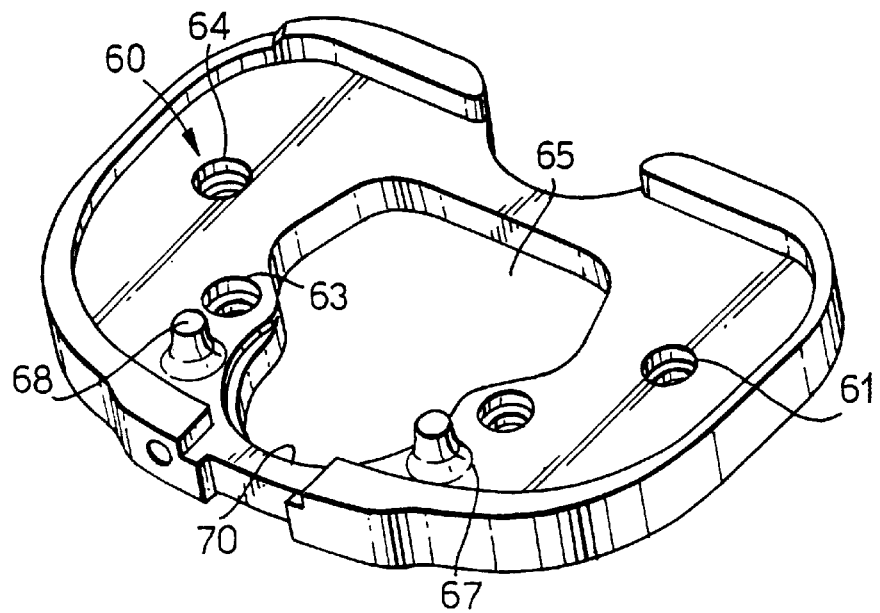
FIG. 6 is a perspective view of a jig for guiding the tibial broach.
Figure 7:
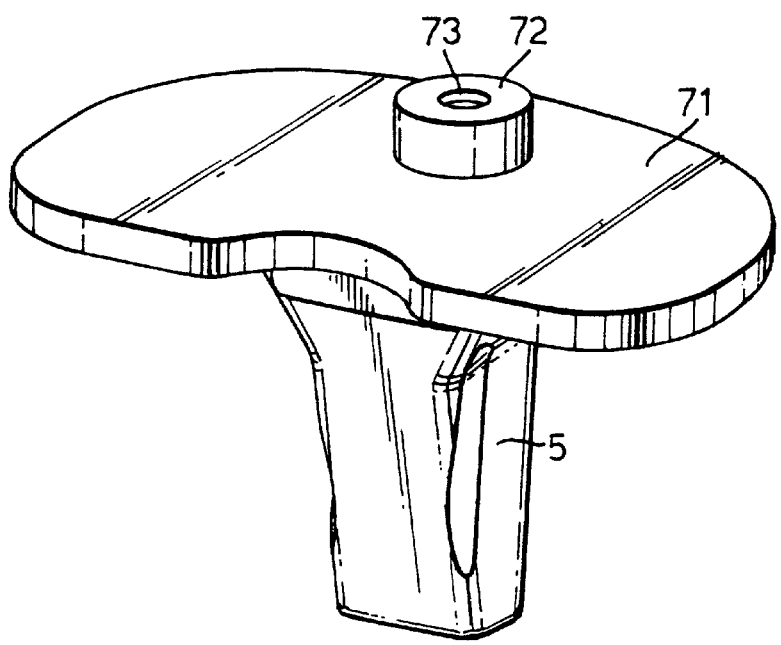
FIG. 7 is a perspective view of a provisional tibial tray.

The next stage is to cut a hole to receive the stem 5 of the provisonal tibial tray (FIG. 7). This can be done using a plate 60 which incorproates a jig for a tibial broach as shown in FIG. 6. However, the preferred procedure is to drill or mill an initial hole to define an anterior surface within the intramedullary canal for the anterior face 5a of the tibial stem (FIG. 2). This hole, which serves as a pilot hole for the subsequent broaching operation, may be cut using the anterior surface 70 of the positioning plate 60 as a guide (FIG. 6). Alternatively, a drilling guide may be placed over the plate 60 (engaging pins 67, 68 or other surface of the tray) to define the position and direction of the hole drilled in the bone.

Figure 5:
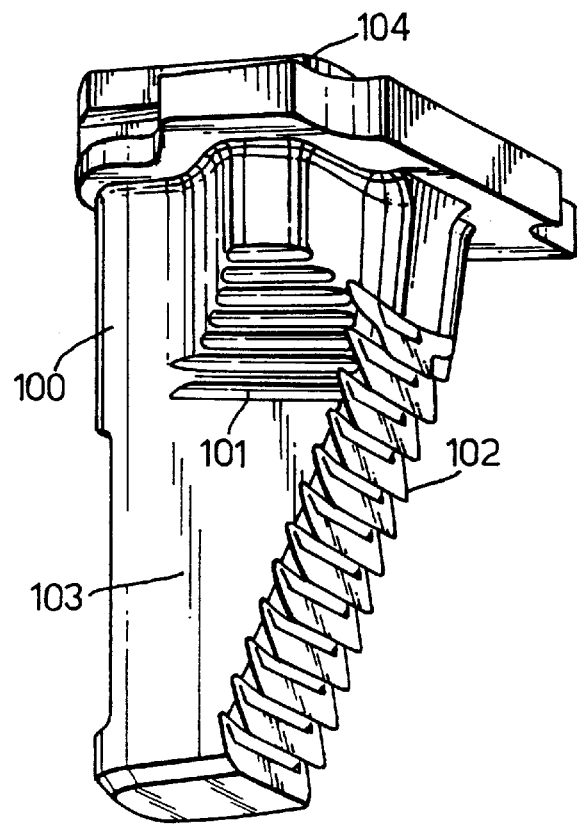
FIG. 5 is a perspective view of a tibial broach from a lateral/posterior direction.

A tibial broach in accordance with the invention is shown in a general perspective view in FIG. 5 and comprises a body 100 having lateral cutting teeth 101 and posterior cutting teeth 102 formed on its medial and lateral surfaces and posterior surfaces, respectively. The body 100 is hollow so that bone removed by the teeth 102 are retained within the hollow centre 103. The top of the broach includes an attachment post 104 which is configured to mate with the female end of a broach handle.

Figure 5A:
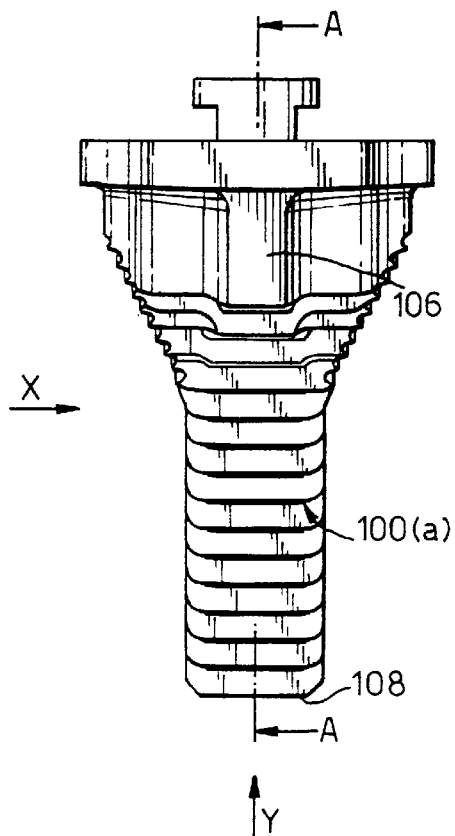
FIG. 5(A) shows an elevation of the broach from the posterior side.
Figure 5B:
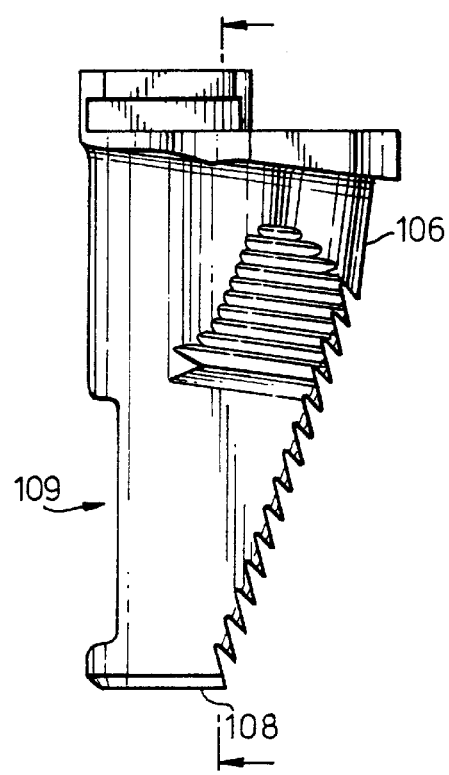
FIG. 5(B) is a side elevation of the broach as seen in the direction of the arrow X in FIG. 5(A)
Figure 5C:
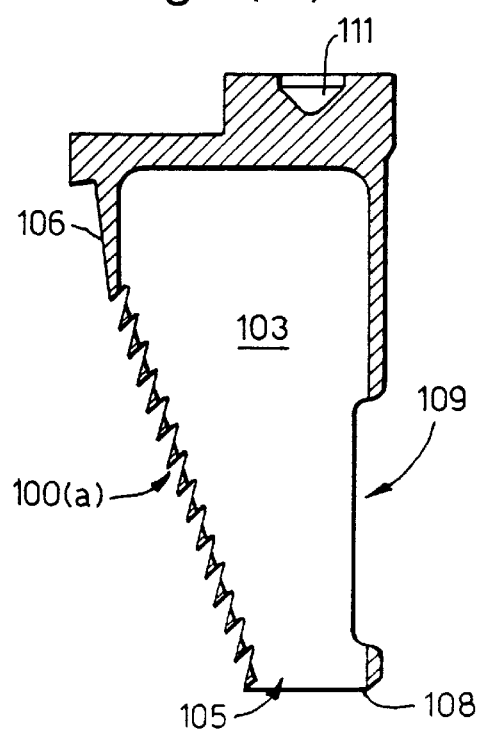
FIG. 5(C) is a section taken on the line A—A in FIG. 5(A)
Figure 5D:
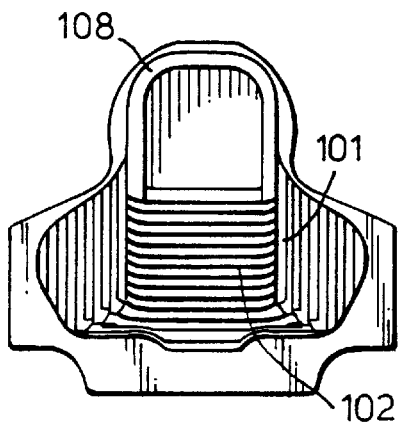
FIG. 5(D) is a view from below, as seen in the direction of arrow Y in FIG. 5(A)
Figure 5E:
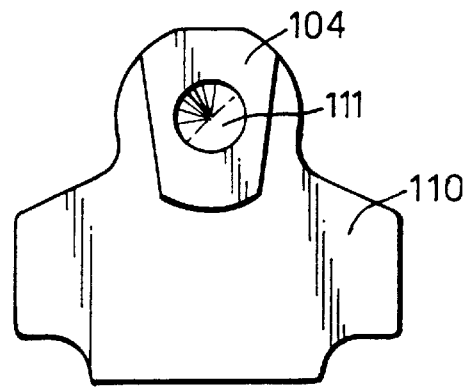
FIG. 5(E) is a view taken from above in FIG. 5(A)
Figure 5F:
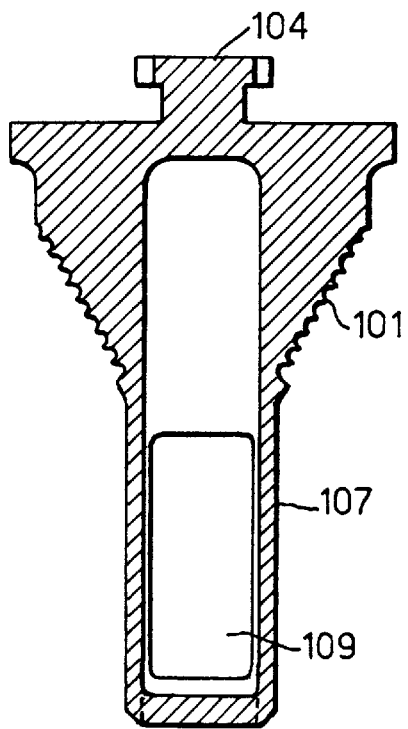
FIG. 5(F) is a section taken on the line B—B in FIG. 5(B)

Further details of the features and construction of the tibial broach are shown in FIGS. 5 and 5(A) to 5(F). Referring to FIG. 5(A), this shows an elevation of the broach from the posterior side of the body (by posterior side we mean the side which is intended to cut the posterior side of the enlarged intramedullary canal). FIG. 5(B) is a side elevation of the broach as seen in the direction of the arrow X in FIG. 5(A) and FIG. 5(C) is a section taken on the line A—A in FIG. 5(A). FIG. 5(D) is a view from below (i.e. as seen in the direction of the arrow Y in FIG. 5(A)) and FIG. 5(E) is a view taken from above in FIG. 5(A) in the opposite direction to the arrow Y. FIG. 5(F) is a section taken on the line B—B in FIG. 5(B).

As can be seen clearly from FIGS. 5(C) to 5(F), the body 100 is substantially hollow and has an internal cavity 103 which is open at its lower end 105 and extends upwards to anvil 104. A series of teeth 102 are formed on the posterior face 100(a) which slopes inwardly and downwardly from a substantially vertical skirt portion 106. As best seen in FIGS. 5(A) and 5(F), the medial and lateral faces of the body 100 are also formed with teeth 101. Teeth 101 are formed on lateral and medial face portions which slope inwardly to meet a lower body portion 107 whose lateral and medial faces are substantially parallel. Teeth 102 are cut in the anterior face in such a way as to provide slots or openings between adjacent teeth in the manner of a rasp. The effect of this is that material cut by the teeth as they are forced downwardly into the intramedullary canal is driven into and is retained within the cavity 103. In contrast, the teeth 101 are formed on the surface of the body 100—see FIG. 5(F). Additional cutting work may be done by the lower edge 108 of the body. An aperture 109 is formed in the posterior face 109 of the body 100. This facilitates removal of cuttings collected in interior space 103. Because mainly soft, cancellous bone is cut as the broach is driven to the bone canal a minimum amount of compression is applied to the bone and the bone which is removed and retained within the cavity 103 is available to the surgeon for grafting purposes. The teeth 101 on the lateral/medial faces of the broach do not communicate with the interior cavity 103 and operate in the manner of a file to adjust the upper portion of the canal which is cut in the bone. As can be seen in FIG. 5(E), the platform 104 projects above the surface of an upper plate 110 which carries identifying indicia giving details of type and size. The platform or post 104 is provided with a depression 111 to which a broach handle is applied to drive the broach into the bone and subsequently remove the broach. The broach handle interacts with a guide which may be attached to the jig 60. This ensures that as the broach is driven into the bone, it cannot twist or depart from the intended direction as determined by a pilot hole.

Thus, after resection of the tibia and establishing the optimum position for the tibial platform using the positioning tray, the jig 60 is fitted in place on the head of the resected tibia using holes 61 to 64 which correspond with the holes 53 to 56 in the tibial positioning tray. Where headless pins are employed, the jig 60 can be attached to the head of the tibia temporarily by placing it over the pins protruding from the head of the tibia. Plate 60 carries upstanding pins 67 and 68 for guiding a drill for cutting the stem. A drill bit may be guided by the surface 70.

Alternatively, a drill guide plate (not shown) is placed over the aperture 65 and is located in proper position by engagement with pins 67, 68 or with other profiled parts of the tray 60. As mentioned above, a drill may be employed to form a pilot hole and which is then cut to final shape with a broach such as described above or with a reamer. The broach is driven into the intramedullary canal by engaging a broach handle with the depression 111 and driving the broach into the tibia using an impactor applied to the broach handle.

Alternatively, drills and reamers may be employed to cut the complete hole for the stem. The plate 60 also includes a guide hole 65 sized to receive the broach and to guide it into the intramedullary canal. Once the canal has been cut, the jig and the broach pins are removed for the final stage of the fitting. This involves the use of a provisional tibial tray having stem as shown in FIG. 7.

The tray shown in FIG. 7 has a stem 5 which corresponds with the stem 5 of the final tibial platform (FIG. 2), and plate 71 which has a periphery corresponding to that of the tibial component. However, the provisional tibial tray has no anterior stop and in place of the guide posts 24 and 25, has a cylindrical boss 72 which includes a threaded hole 73. A provisional plastics component can be placed over the boss 72 and the articulation of the joint tested with the femoral component.

The surface of the platform 71 may be marked with guidance lines in the area anteriorly of the boss 72, so that the surgeon can check whether the meniscal component has the correct movement in the anterior direction. Using the provisional tibial tray, the surgeon can test the articulation and movement of different meniscal components, or alter the tension of non-resected ligaments to achieve the optimum arrangement.

We claim:

1. A provisional instrument component for evaluating the fit of a knee replacement prosthesis on a resected tibial surface, said component comprising a positioning tray having a peripheral profile corresponding to that of a tibial platform of the prosthesis, the tray having an upper surface and an under surface which is substantially flat and free from projections and said tray having a plurality of holes for receiving pins for temporarily attaching the positioning tray in a desired position on said resected tibial surface, wherein a boss is carried on the upper surface of the tray for guiding a temporary plastics meniscal bearing component on said upper surface with freedom of movement in the anterior-posterior direction.

2. An instrument kit for fitting and evaluating the fit of a knee replacement prosthesis on a resected tibial surface, which comprises a tibial sizing and positioning tray having a plurality of holes therein for receiving pins for temporarily attaching the positioning tray in a desired position on said resected tibial surface and a jig for a tibial broach having a peripheral profile which corresponds with said positioning tray and having locating holes which correspond with the holes in said positioning tray, the jig also having an aperture which is shaped to guide the broach, the positioning tray having a peripheral profile corresponding to that of the tibial platform of the prosthesis, the tray having an upper surface and an under surface which is substantially flat and free from projections.

3. A tibial broach which comprises a hollow body having an upper end and a lower end, the hollow body being closed at its upper end and having an open lower end whose edges are sharpened, said hollow body having an anterior face and a posterior face which slopes downwardly and inwardly towards said lower end, wherein said posterior face is formed with a series of teeth adapted to cut bone on driving the broach into a tibia, said posterior face having apertures permitting bone cut by the teeth to enter the hollow body.

4. A broach as claimed in claim 3 wherein said hollow body has substantially parallel lower lateral and medial faces and upper lateral and medial faces which slope upwardly and outwardly towards the upper end of the lower body, the upper lateral and medial faces being formed with cutting teeth.

* * * * *